United States Patent

Hsu et al.

Patent Number: 5,352,837
Date of Patent: Oct. 4, 1994

[54] PROCESS FOR THE PREPARATION OF 3-(METHYLTHIO)PROPANAL

[75] Inventors: Yung C. Hsu, Chesterfield; Dennis A. Ruest, Manchester, both of Mo.

[73] Assignee: Novus International, Inc., Chesterfield, Mo.

[21] Appl. No.: 73,763

[22] Filed: Jun. 8, 1993

[51] Int. Cl.$^5$ .................. C07C 323/50; C07C 323/51
[52] U.S. Cl. ..................................... 568/41; 568/38; 568/39; 568/42
[58] Field of Search ................ 568/20, 39, 63, 41, 568/42, 38

[56] References Cited

U.S. PATENT DOCUMENTS

| | | | |
|---|---|---|---|
| 2,542,768 | 2/1951 | Gresham et al. | 260/465.6 |
| 2,564,105 | 8/1951 | Gresham et al. | 260/465.6 |
| 2,626,282 | 1/1953 | Cunningham et al. | 260/601 |
| 2,676,190 | 4/1954 | Bernard et al. | 260/601 |
| 2,776,996 | 1/1957 | Hunt et al. | 260/601 |
| 3,438,868 | 4/1969 | Sawaki et al. | 203/8 |
| 3,529,940 | 9/1970 | Shima et al. | 23/288 |
| 3,833,651 | 9/1974 | Ouchi et al. | 260/534 S |
| 3,878,057 | 4/1975 | Mannnsfeld | 203/35 |
| 4,048,232 | 9/1977 | Koberstein et al. | 260/601 R |
| 4,225,516 | 9/1980 | Biola et al. | 568/41 |
| 4,319,047 | 3/1982 | Komorn et al. | 568/41 |
| 5,155,262 | 10/1992 | Etzkorn et al. | 562/532 |
| 5,183,936 | 2/1993 | Etzkorn et al. | 562/532 |
| 5,198,578 | 3/1993 | Etzkorn et al. | 562/532 |

FOREIGN PATENT DOCUMENTS

| | | |
|---|---|---|
| 797873 | 10/1968 | Canada . |
| 820968 | 8/1969 | Canada . |
| 2314917 | 1/1970 | France . |
| 48-56144 | 11/1973 | Japan . |
| 6809647 | 1/1970 | Netherlands . |
| 85095 | 10/1984 | Romania . |
| 1150252 | 4/1969 | United Kingdom . |
| 1162054 | 8/1969 | United Kingdom . |
| 1166961 | 10/1969 | United Kingdom . |
| 1173174 | 12/1969 | United Kingdom . |
| 1177470 | 1/1970 | United Kingdom . |

*Primary Examiner*—Werren B. Lone
*Attorney, Agent, or Firm*—Senniger, Powers, Leavitt & Roedel

[57] ABSTRACT

A process for the continuous preparation of 3-(methylthio)propanal. A liquid reaction medium is contacted with a gaseous acrolein feed stream in a gas/liquid contact zone. The reaction medium contains 3-(methylthio)propanal, methyl mercaptan and a catalyst for the reaction between methyl mercaptan and acrolein. The gaseous acrolein feed stream comprises acrolein vapor and non-condensable gas. Acrolein is transferred from the acrolein feed stream to the reaction medium and reacts with methyl mercaptan in that medium to produce a liquid reaction product containing 3-(methylthio)propanal. The non-condensable gas is separated from the liquid reaction product. The reaction product is divided into a product fraction and a circulating fraction, and the circulating fraction is recycled to the gas/liquid contact zone.

36 Claims, 3 Drawing Sheets

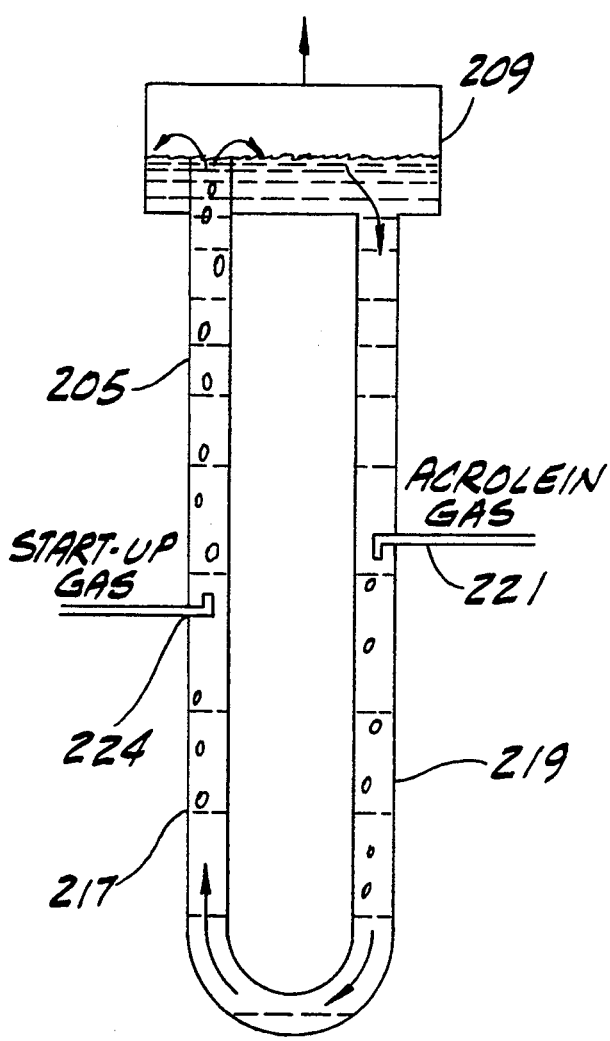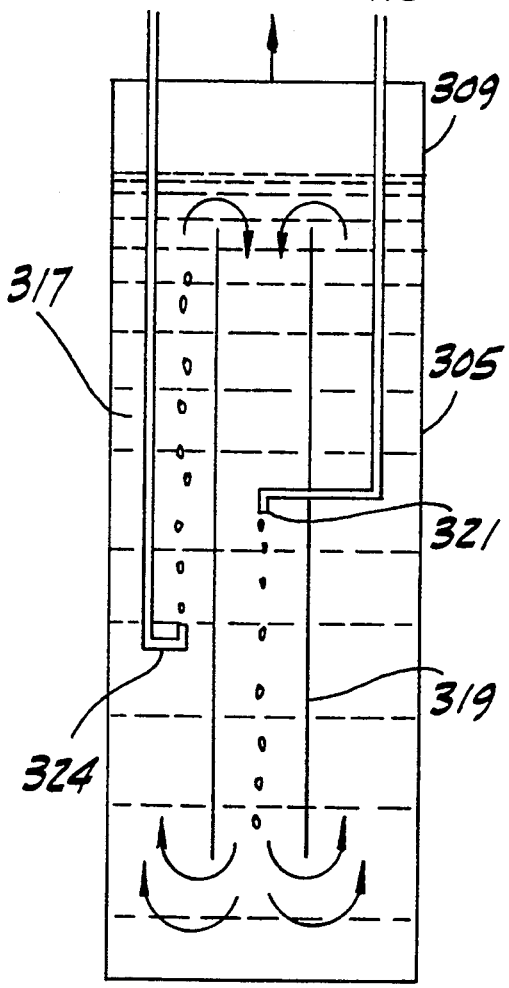

PROCESS FOR THE PREPARATION OF 3-(METHYLTHIO)PROPANAL

BACKGROUND OF THE INVENTION

This invention relates to the preparation of 3-(methylthio)propanal, and more particularly to a continuous process for the direct manufacture of 3-(methylthio)propanal in a gas/liquid reaction system.

3-(Methylthio)propanal (hereinafter "MMP") is an intermediate for the manufacture of both d, 1-methionine and 2-hydroxy-4-(methylthio)butanoic acid ("HMBA"). Methionine is an essential amino acid in which components of the animal feed compositions are commonly deficient. HMBA provides a source of methionine, and is widely used as a methionine supplement in animal feed formulations. MMP relatively free of impurities is typically required for the manufacture of HMBA or methionine.

MMP is produced by reaction of acrolein with methyl mercaptan. In a conventional process for the preparation of MMP, liquid acrolein and methyl mercaptan are introduced into a reactor containing liquid phase MMP product. Reaction takes place in the liquid phase. In order to produce MMP of desired quality, refined acrolein is used in the process, and/or the MMP product is distilled before use in the manufacture of either HMBA or methionine.

Acrolein is a highly toxic and flammable material. It is conventionally prepared by vapor phase oxidation of propylene over a solid phase catalyst, producing a crude gaseous reaction product which contains water vapor, acrylic acid, acetaldehyde, and other organic by-products. Typically, the gas is treated to remove acrylic acid, then contacted with refrigerated water for absorption of acrolein. The resultant aqueous solution is distilled to recover the absorbed acrolein and other organic components. The crude acrolein is then refined to reject lower boiling impurities such as acetaldehyde, producing a purified liquid acrolein product. The refined liquid acrolein is stored for use in the manufacture of MMP.

Storage of liquid acrolein involves significant toxicity, fire and explosion hazards. High capital and operating costs are consequently incurred in providing for the safe handling of this material. The cost of handling acrolein could be substantially reduced if gas phase acrolein were transferred directly and continuously from the acrolein manufacturing process to the MMP reactor without storage or condensation. However, since the conventional commercial processes for the preparation of MMP involve liquid phase reactions, the need to condense the gaseous acrolein product has been considered unavoidable. Moreover, because the conventional process typically uses a batch reaction system, condensation and in-process storage of liquid acrolein is necessary as a surge buffer between operation of the acrolein process and the MMP reactor.

U.S. Pat. No. 4,225,516 describes a continuous process for the manufacture of MMP from the acrolein product gas obtained in the catalytic oxidation of propylene. In this process, the gas is first treated for removal of acrylic acid, then cooled to condense water vapor. To reduce the water vapor content to a level acceptable in the MMP reaction, the final condensation temperature is 0° to −5° C. The treated and cooled acrolein gas stream is contacted with a stream of liquid MMP in a countercurrent absorption tower, resulting in absorption of acrolein in the MMP. The MMP liquid stream containing dissolved acrolein is circulated to an MMP reactor where methyl mercaptan is added. The process proceeds by reaction of methyl mercaptan with MMP to form the hemimercaptal of MMP, and the hemimercaptal in turn reacts with acrolein in the liquid phase to produce additional MMP. Thus, the process requires the presence of up to 1% by weight of the hemimercaptal in the reaction mixture. MMP product withdrawn from the system at a rate equivalent to MMP production in the reactor, while the bulk of the MMP stream is recirculated to the acrolein absorber.

To provide for quantitative absorption of acrolein in MMP, the '516 patent requires cooling the circulating MMP to a temperature 0° to −15° C. before it enters the absorber. The refrigeration required for condensing water vapor at 0° to −5° C. and cooling MMP to as low as −15° C. contributes substantially to the capital and operating expense of the '516 patent process. Moreover, because the reaction proceeds through formation of the hemimercaptal, the kinetics of the conversion reaction are relatively slow, resulting in less than desirable productivity and thus further adding to the cost of operation of the process.

Although sub-zero absorption increases acrolein recovery at equilibrium, it also increases the absorption of impurities, such as acetaldehyde, in the MMP product. Moreover, since the scrubber is separate from the reactor, acrolein absorbed in the scrubber is not consumed immediately in the absorption zone. As a consequence, acrolein tends to accumulate in the liquid phase, which decreases the driving force for mass transfer. The high concentration of acrolein in MMP liquid also increases the possibility of forming by-products from reactions between acrolein and MMP.

SUMMARY OF THE INVENTION

Among the several objects of the present invention are the provision of an improved process for the preparation of MMP; the provision of such a process which can be operated in a continuous mode; the provision of such a process which can be operated with high productivity; the provision of such a process which can be operated with a relatively crude acrolein raw material; the provision of such a process which does not require refrigeration for absorption or condensation of acrolein; the provision of such a process which eliminates the need for storage of liquid acrolein, in particular, the provision of such a process which can be operated using a gaseous acrolein feed obtained directly from the continuous oxidation of propylene, without intermediate condensation of liquid acrolein; and the provision of such a process which can produce high quality MMP for direct use in the preparation of methionine or HMBA without the need for further purification.

Briefly, the present invention is directed to a process for the continuous preparation of 3-(methylthio)propanal. The process comprises contacting a liquid reaction medium with a gaseous acrolein feed stream in a gas/liquid contact zone. The reaction medium contains 3-(methylthio)propanal, methyl mercaptan, and a catalyst for the reaction between methyl mercaptan and acrolein. The gaseous acrolein feed stream comprises acrolein vapor and non-condensable gas. Acrolein is transferred from the feed stream to the reaction medium and reacts with methyl mercaptan in the medium to produce a liquid reaction product containing 3-(methylthio)- propanal. Noncondensable gas is separated from the liquid reaction product and the reaction product is divided into a product fraction and a circulating fraction. The circulating fraction is recycled to the gas/liquid contact zone.

Other objects and features will be in part apparent and in part pointed out hereinafter.

BRIEF DESCRIPTION OF THE DRAWINGS

FIG. 3 is a schematic illustration of a gas lift reactor adapted for operation at low pressure drop;

FIG. 4 is a schematic illustration of a draft tube type gas lift reactor adapted for operation at low pressure drop.

DESCRIPTION OF THE PREFERRED EMBODIMENTS

In accordance with the present invention, MMP is produced from methyl mercaptan and a gaseous acrolein feed stream in a gas/liquid reaction system comprising liquid MMP. In a gas/liquid contact zone, a liquid phase containing MMP and catalyst is contacted with methyl mercaptan and a gas containing acrolein and non-condensables. Acrolein is transferred from the gas phase to the liquid phase, and reacts directly with methyl mercaptan in the liquid phase to produce additional MMP. Exothermic reaction heat is removed to a heat transfer fluid flowing through heat transfer means, such as a jacket or coil, in contact with the gas/liquid contact zone.

In the gas/liquid contact zone, high mass transfer coefficients are provided by intimate gas/liquid contact, and the driving force for mass transfer is preferably maximized by maintaining substantially plug flow in the gas phase. Intimate gas/liquid contact may be realized by operating in a turbulent flow range, which may be characterized, for example, by relatively high superficial gas and liquid velocities in a bubble flow regime, wherein bubbles are actively coalescing and breaking up as a result of the turbulence. Such turbulent conditions also promote high rates of heat transfer from the gas/liquid contact zone to a jacket or coil in heat transfer communication with the contact zone. Alternatively, gas/liquid contact may be effected by countercurrent flow of gas and liquid within the contact zone. In the latter embodiment of the invention, reaction heat is advantageously transferred to a cooling fluid in an external heat exchanger through which the MMP reaction medium is circulated.

By maintaining substantially equimolar addition of methyl mercaptan and acrolein to the reaction medium, formation of the hemithioacetal of MMP is substantially avoided. As a consequence, the methyl mercaptan and acrolein react directly to form MMP. Since this reaction path is much faster than the reaction which proceeds through formation of the hemithioacetal, the rate of reaction is 3 to 10 times higher than that obtained in a process of the type described in the '516 patent. At such reaction rates, the rate of conversion is limited by the rate of mass transfer of acrolein from the gas phase to the liquid phase. However, it has been found that, when turbulent conditions are maintained in accordance with the preferred embodiments of the invention, high coefficients of mass transfer are realized. Moreover, because of the direct rapid reaction between acrolein and methyl mercaptan in the liquid phase, acrolein entering the liquid phase is consumed immediately, thereby enhancing the driving force for mass transfer. Thus, overall mass transfer rates are high. The combined effect of direct reaction and high mass transfer rates affords high productivity in the reaction system of the invention.

Figure 1:
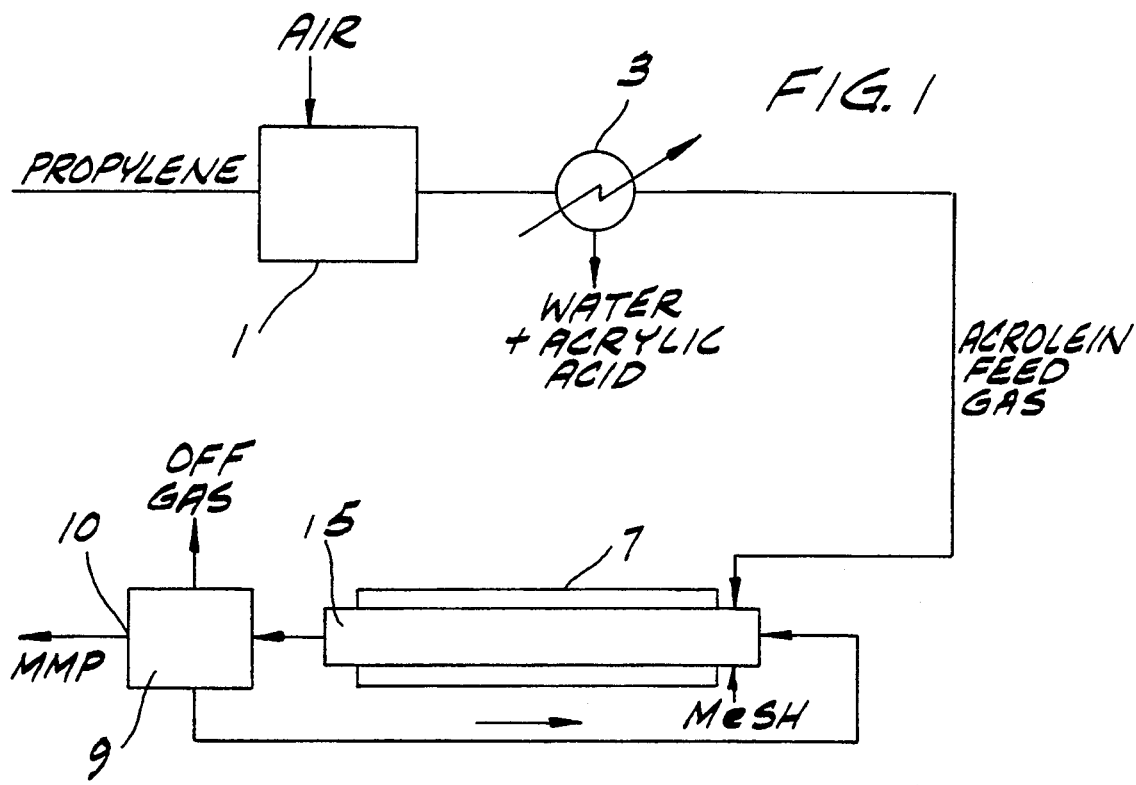
FIG. 1 is a schematic flowsheet of the process of the invention, illustrating continuous manufacture of MMP from a crude gaseous acrolein product obtained from the continuous catalytic oxidation of propylene.

Referring to FIG. 1, acrolein is continuously generated by catalytic oxidation of propylene in an acrolein reactor 1. The crude acrolein product gas exiting the reactor contains about 4% to about 10% by volume acrolein, between about 0.4% and about 1.0% by volume acrylic acid, up to about 0.6% by volume propylene, up to about 0.6% by volume propane, up to about 0.5% by volume propionaldehyde, between about 0.1% and about 0.2% by volume acetaldehyde, and between about 40% and about 50% by volume water vapor, and between about 40% and about 50% by volume non-condensables, including oxygen, nitrogen, carbon monoxide and carbon dioxide. The crude product gas is cooled in an indirect heat exchanger 3, causing condensation of acrylic acid and water from the crude gas product, and providing a cooled acrolein feed gas stream containing between about 5% and about 25%, more commonly between about 7% and about 15%, by volume acrolein, up to about 0.1% by volume acrylic acid, up to about 1.0% by volume propylene, up to about 1.0% by volume propane, up to about 1.0% by volume propionaldehyde, up to about 0.5% by volume acetaldehyde, between about 2 and about 8% by volume water vapor, and between about 60% and about 80% by volume non-condensables. Optionally, acrylic acid may be initially removed from the crude acrolein product gas, by contacting the gas with a conventional absorbing agent in a countercurrent contacting unit, such as a packed tower. Gas exiting the absorber may be further cooled for condensation of water vapor by passing the gas through an indirect heat exchanger downstream of the absorber.

The cooled acrolein feed gas stream is then introduced into a reaction medium, comprising a circulating stream of MMP, in a continuous flow reactor 5. Reactor 5 is provided with a cooling jacket 7. The circulating MMP contains a catalyst for the reaction of methyl mercaptan and acrolein. Methyl mercaptan is introduced into the MMP circulating stream at any convenient point, but is preferably introduced together with the acrolein, or slightly upstream of the point at which acrolein is introduced. Thus, a two phase reactant mixture is prepared, in which acrolein is distributed between a liquid phase containing MMP and catalyst, and a gas phase containing non-condensables. Methyl mercaptan may also be distributed between the two phases, but is observed to be substantially dissolved in the liquid phase. The catalyst is typically an organic acid salt of an amine. In the gas/liquid contact zone, which extends downstream from the point of introduction of acrolein, acrolein is progressively transferred from the gas phase to liquid phase, and reacts directly and continuously with methyl mercaptan in the liquid phase to produce MMP. To the extent that methyl mercaptan is initially distributed between the phases, it is also progressively transferred to the liquid for reaction with acrolein.

Turbulent flow conditions are maintained in the gas/liquid contact zone, preferably by establishing a two phase flow velocity in the turbulent region, as defined above. Reaction progresses rapidly to produce a two phase reaction product mixture, comprising a liquid phase containing MMP product and catalyst, and a gas phase containing non-condensables. The reaction product exiting the reactor is introduced into a separator 9 where the gas phase and liquid phase are allowed to separate. The gas phase, which contains propane, propylene, propionaldehyde, acetaldehyde, and water vapor, is vented from the separator to an emissions control device, such as an incinerator. Net production of MMP is removed from the separator via a product port 10, while the bulk of the MMP is recirculated from the separator to the reactor. The MMP product is substantially free of methyl mercaptan, acrolein and the impurities contained in the acrolein feed gas. Without need for further purification, the MMP product may be used as an intermediate in the manufacture of HMBA.

The reaction may be carried out at a temperature between about 30° C. and about 70° C., preferably between about 40° C. and about 50° C., and at a total pressure of between about 1 and about 2 atmospheres. Methyl mercaptan and acrolein are introduced into the reaction medium in a mercaptan to acrolein molar ratio of between about 0.95 and about 1.2, but most preferably between about 1.00 and about 1.02. As noted, the acrolein feed contains between about 5% and about 25% by volume, more typically between about 7% and about 15% by volume. Most preferably the acrolein vapor feed stream contains between about 10% and about 15% by volume acrolein.

At reaction temperatures below about 50° C., the favorable acrolein equilibrium between the liquid and gas phases provides a particularly effective driving force for mass transfer to the liquid phase, but at temperatures significantly below 40° C. a refrigerated coolant fluid may be necessary, and the kinetics of reaction may begin to limit productivity. Moreover, at cooler reaction temperatures the equilibrium distribution of acetaldehyde between the gas and liquid phases also becomes unfavorable, resulting in an increased concentration of acetaldehyde in the product exiting the separator. An especially preferred temperature for the reaction is between about 40° C. and about 45° C. In this range, the reaction temperature can be readily controlled by transfer of heat from the reacting mixture to cooling tower water at up to 35° C. flowing through a jacket surrounding the gas/liquid contact zone. As the reaction consumes dissolved acrolein, additional acrolein is progressively transferred from the gas to the liquid phase in response to the disequilibrium caused by the acrolein consumption. Consequently, in most embodiments of the present invention, refrigeration is not needed or desired for either controlling the reaction temperature or promoting transfer of acrolein from the gas to the liquid phase.

Although high pressure also favors mass transfer, rapid mass transfer is achieved at or near atmospheric pressure in a turbulent gas/liquid contact zone, so that the use of high pressure reactor vessels is not necessary. Moreover, by maintaining the reactor at moderate pressure levels, the pressure prevailing in the propylene oxidation reactor may be sufficient for introduction of the acrolein product gas into the MMP reactor without the need for mechanical compression of the gas.

While it is feasible to operate with a gas feed stream having an acrolein content ranging between about 5% and about 25% by volume, the rate of mass transfer is enhanced if the feed gas contains at least about 10% by volume acrolein. On the other hand, too high an acrolein content may overload the absorptive capacity of the gas/liquid contact zone, and may have an adverse effect on both recovery of acrolein from the gas phase and yield of MMP based on acrolein. Further balancing the immediate needs of the present process with factors bearing on the operation of a typical acrolein reactor, a feed gas concentration of between about 10% and about 15% by volume acrolein may be considered optimal.

By establishing a very slight excess of mercaptan in the reactant mixture, conversion of acrolein is maximized and the need for disposition of unreacted acrolein is essentially obviated. Where the molar ratio of reactants is controlled in the range of between about 1.00 and about 1.02 moles methyl mercaptan per mole of acrolein, direct reaction between the mercaptan and acrolein is effected in preference to formation of the intermediate hemi(methylthio)acetal of MMP. As a consequence, a high rate of reaction is realized, with high productivity and relatively low capital and operating expense of the reactor. The reactant ratio may be controlled by various means known to the art. Preferably, the circulating MMP stream is periodically analyzed by gas chromatography downstream of the gas/liquid contact zone, and any necessary adjustments are made in the relative acrolein and methyl mercaptan feed rates to make certain that the proper excess of methyl mercaptan is maintained and formation of the hemithioacetal avoided. An in-line analyzer may be used for this purpose. Except during Startup, the process is operated in a continuous recirculating steady state mode. Accordingly, the addition ratio of methyl mercaptan to acrolein can be adjusted to essentially to 1.0 as soon as steady state conditions are achieved.

Conventional catalysts and catalyst concentrations may be used for the reaction. Such catalysts include a wide variety of organic amines such as, for example, pyridine, hexamethyltetraamine, or triethylamine. Organic acids are typically included to inhibit polymerization of acrolein. Where, for example, a pyridinium acetate catalyst is used, the concentration is maintained at between about 0.2 and about 1.0%, preferably between about 0.35 and about 0.5%, by continuous or periodic additions of catalyst to the liquid phase.

The rate of MMP circulation is at least an order of magnitude greater than the rate of production of MMP, preferably between about 20 and about 50 times greater, so that the reactor is essentially backmixed in the liquid phase. Any of a variety of two phase reactors may be used in the reaction, e.g., a wetted-wall column, a pipeline reactor, a stirred tank, a bubble column, a packed column or a tray column. To promote rapid mass transfer, the gas phase is preferably in plug flow. In plug flow an acrolein concentration gradient in the gas phase is established and maintained along the reactant flow path in the gas/liquid contact zone, thereby providing an integrated average driving force for mass transfer substantially greater than that which prevails when the gas phase is backmixed. A gas lift reactor is particularly preferred because it may be operated in gas phase plug flow, and because the substantial volume of non-condensables in the acrolein gas feed stream can be used to advantage both for circulation of the MMP liquid phase and to produce excellent liquid mixing in the reactor. Thus, the need for mechanical moving parts, such as pumps or agitators, is eliminated. Alternatively, a tray column may be used to particular advantage, especially where there is a need to minimize pressure drop through the gas/liquid contact zone.

Figure 2:
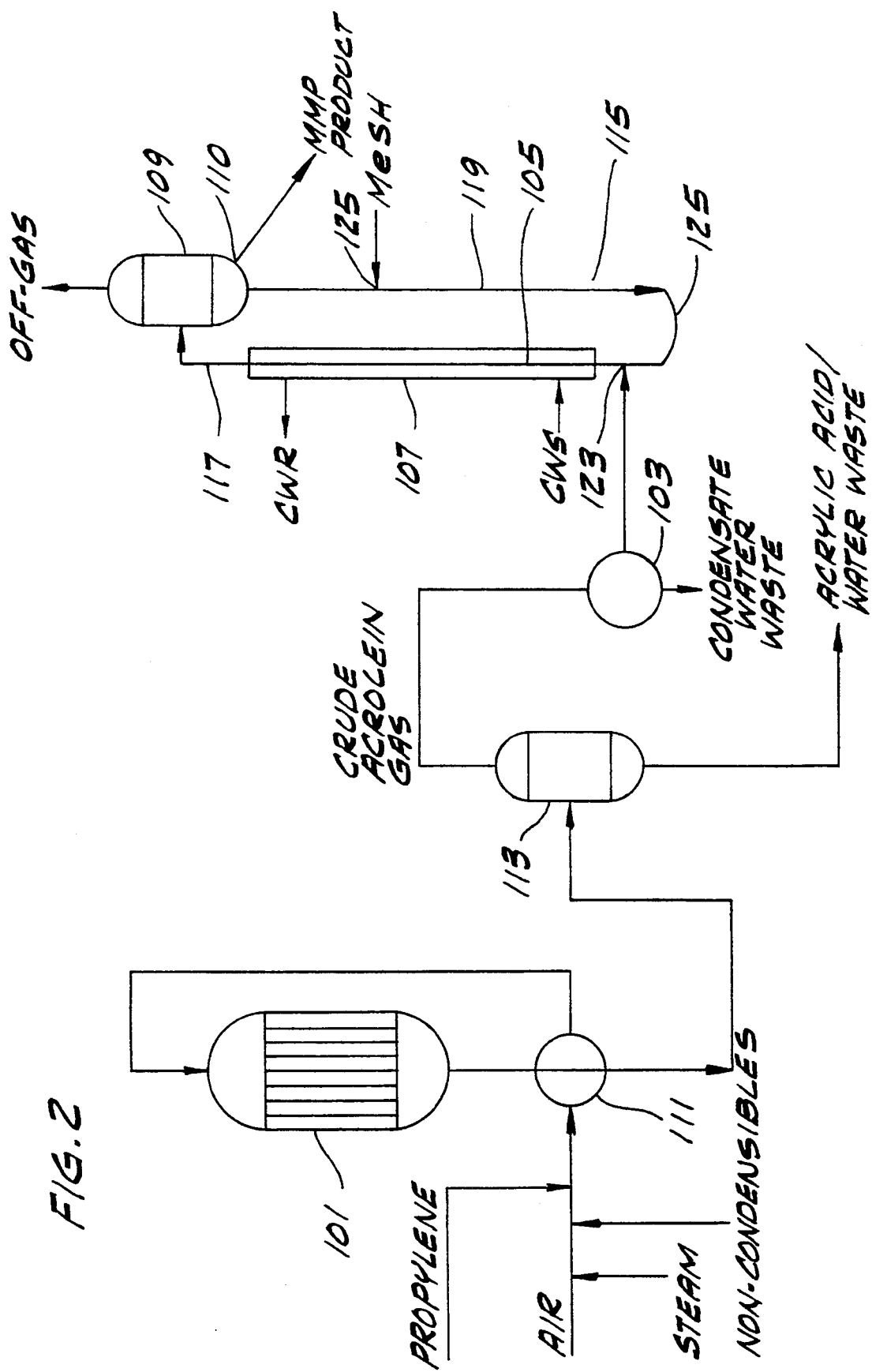
FIG. 2 is a schematic illustration of a preferred process of the invention in which MMP is produced from methyl mercaptan and acrolein in a turbulent gas lift reactor.

Illustrated in FIG. 2 is a loop type gas lift reactor apparatus of the invention and its use in an integrated process in which crude gas phase acrolein is cooled and introduced directly into the MMP reactor. In the integrated process as illustrated, propylene is mixed with air and introduced together with diluent steam and/or non-condensable gases into a reactor 101 containing a catalyst for the oxidation of propylene to acrolein. A reactor feed stream is prepared by mixing air and propylene with diluents as noted, and this mixture is preheated in an indirect heat exchanger 111 by transfer of heat from the crude acrolein product gas. In a countercurrent flow packed tower absorber 113, the partially cooled product gas is contacted with a liquid absorbing medium for removal of acrylic acid from the gas stream. Gas exiting the absorber is passed through another indirect heat exchanger 103 for further cooling of the product gas and condensation of acrylic acid and water vapor therefrom. Optimally, and preferably, acrylic acid and excess water vapor are removed by condensation alone, obviating the need for the acrylic acid absorber and the pressure drop required for gas flow through the absorber. The cooled acrolein product gas is then introduced into the gas lift reactor 115.

Reactor 105 comprises an upward flow conduit ("upleg") 117 provided with a jacket 107 through which a cooling fluid may be circulated. The reactor further comprises a downflow conduit ("downleg") 119 which is in fluid flow communication with the upleg through a bottom loop 121. Upleg 117 comprises the gas/liquid contact zone. Between and in fluid flow communication with the upper ends of the two legs is a separator 109. In a commercial unit, desired capacity may be provided by the use of multiple reactor loops, in combination with a single separator. Upleg 117 includes a gas inlet 123 at the lower end thereof for introduction of cooled acrolein feed gas, and downleg 119 has a fluid inlet 125 for introduction of vapor or liquid methyl mercaptan. Alternatively, the methyl mercaptan can be introduced at or near the point of introduction of acrolein feed gas. The upleg comprises the gas liquid contact zone and is sized so that two phase flow is in the bubble flow regime, wherein the gas is dispersed in the form of discrete bubbles within a continuous liquid phase, or at the margin between bubble flow and slug flow. Liquid circulation is induced by the liquid head differential resulting from the lower density of the two phase fluid contained in the upleg as compared to the liquid in the downleg. To establish the preferred flow conditions, the superficial gas velocity in the upleg is adjusted to between about 0.1 and about 0.5 m/sec. At such combination of gas velocity and reactor height, the gas holdup in the upleg is between about 5% and about 20%, and the superficial liquid velocity in the upleg is between about 0.3 and about 3.0 m/sec. To provide for the desired rate of circulation, the height of the gas lift loop is preferably between about 20 feet and about 30 feet, requiring the gas pressure at the gaseous acrolein feed inlet to the reactor to be between about 10 and about 15 psig, i.e., between about 67 and about 100 kPa gauge. Optionally, a pump may be provided in bottom loop 121 to assist in circulation and lower the requisite height of upleg 117.

To start up the reactor of FIG. 2, the circulating loop is substantially filled with MMP, after which introduction of acrolein feed gas and methyl mercaptan can be immediately commenced. Even at ambient temperature, the reaction proceeds at a sufficiently rapid rate so that exothermic heat of reaction rapidly brings the reactant mixture to the preferred 40° C.+ temperature at which steady state operations are conducted.

Using a gas lift reactor, the process of the invention can be operated to provide an acrolein recovery of at least about 98%, a conversion of at least about 97%, and an acrolein yield of at least about 95%. Recovery is defined as the proportion of acrolein entering in the feed gas that is transferred to the liquid phase; conversion is defined as the proportion of entering acrolein which is consumed in the reaction; and yield is defined as the proportion of the acrolein in the feed gas which is converted to net product MMP.

When the process of the invention is operated in tandem with a facility in which acrolein is produced by catalytic oxidation of propylene, no increase in by-product formation or MMP product degradation is incurred as a result of the presence of impurities such as propylene, propane, acetaldehyde, propionaldehyde, oxygen, carbon monoxide, carbon dioxide, in the acrolein feed gas. Thus, the process can be economically integrated with an acrolein manufacturing facility to avoid the need for condensation of acrolein, purification of acrolein, or storage of acrolein in liquid form. The process is particularly adapted for use in combination with an acrolein manufacturing process in which the crude acrolein product gas comprises a mixture of acrolein vapor and inert gases containing low concentrations of water vapor and organic impurities.

Where a loop type gas lift reactor is used, the back pressure resulting from pressure drop in the upleg may tend to raise the pressure in the acrolein reactor to a level higher than optimum. This backpressure is at least partially offset by elimination of the acrolein absorber used in the preparation of refined liquid acrolein. Pressure drop across the absorber imposes back pressure on the reactor in a conventional acrolein process. Moreover, any adverse effect of pressure drop in a gas lift reactor may be avoided by any of a number of stratagems. For example, a modest negative pressure may be imposed on the separator 109 by placing a compressor in the gas vent line from the separator. As noted above, the requisite height of the gas/liquid contact zone may be reduced by mechanical circulation of the MMP reaction medium.

Illustrated in FIG. 3 is an alternative gas lift reaction system which is adapted for operation at especially low gas pressure drop. Instead of introducing acrolein gas near the bottom of the upleg, as in FIG. 2, the gaseous acrolein feed stream is introduced through an inlet 221 in downleg 219. Circulation in the gas lift reactor loop is initiated on startup by introduction of a startup gas through an inlet 224 in upleg 217. The elevation of the startup inlet is at least slightly lower than that of inlet 221, but both may be located as high as necessary in the gas loop so that liquid head in the loop does not create excessive backpressure at the point of gas introduction. Either the acrolein feed gas or an inert gas may be used for startup. Once circulation of the MMP reaction medium has been established, introduction of acrolein feed gas may be commenced through inlet 221, and introduction of startup gas terminated as soon as two phase flow extends from inlet 221 to inlet 224 or above. The gas liquid contact zone comprises the portion of downleg 219 below inlet 221 plus the entire upleg 217. Because the component of two phase zone in leg 217 is longer than that in leg 219, downward flow of the two phase reactant mixture is maintained in leg 219. The reactor then continues to operate with a liquid head differential determined by the liquid head above inlet 221. Where that liquid head is modest, pressure drop is minimized. If pressure drop limitations on permissible liquid head differential cause the superficial liquid velocity to be less than optimum for effective mass transfer, this can be compensated for by increasing the vertical dimension below the gas entry point to increase the residence time for mass transfer.

In another alternative, a draft tube type gas lift reactor may be used in which the acrolein feed gas is introduced into the draft tube. Such a system is illustrated in FIG. 4. The reactor 305 comprises a draft tube 319 radially centered in a cylindrical reaction vessel 320 and comprising the downleg of a gas lift reactor system. The annular region between draft tube 319 and the inside wall of reactor vessel comprises an upleg 317, and together the draft tube and annular region comprise a circuit for circulation of MMP. Gaseous acrolein feed stream is introduced through a dip pipe inlet 321 in draft tube 319. Circulation in the gas lift reactor loop is initiated on startup by introduction of a startup gas through an inlet 324 in annular upleg 317. Though shown as a dip pipe with a single outlet, inlet 324 is preferably a ring type sparger surrounding the draft tube, with outlets spaced around its entire periphery. As in the reactor of FIG. 3, the elevation of the startup inlet is at least slightly lower than that of inlet 321, and both may be located at whatever elevations are necessary to minimize backpressure. Circulation is commenced in the same manner as described above with respect to FIG. 3, after which introduction of acrolein feed gas may be commenced through inlet 321, and introduction of startup gas terminated as soon as two phase flow extends from inlet 321 to inlet 324. The longer two phase zone in the annular leg 317 maintains downward flow of the two phase reactant mixture in the draft tube. The reactor then continues to operate with a liquid head differential determined by the liquid head above inlet 321. Without significantly affecting the gas pressure drop, the vertical dimension of the draft tube below the dip tube outlet may be as large as necessary to provide adequate residence time for mass transfer. Reaction heat may be removed from the reactor of FIG. 3 via a jacket surrounding the reactor 305 or a coil or other heat transfer surface disposed within the reactor. Except for the superficial liquid velocity and residence time in those instances where liquid head differential is minimized to avoid excessive backpressure on the acrolein reactor, the preferred operating conditions for the reactor of FIG. 3 are substantially the same as those in FIG. 2.

Figure 5:
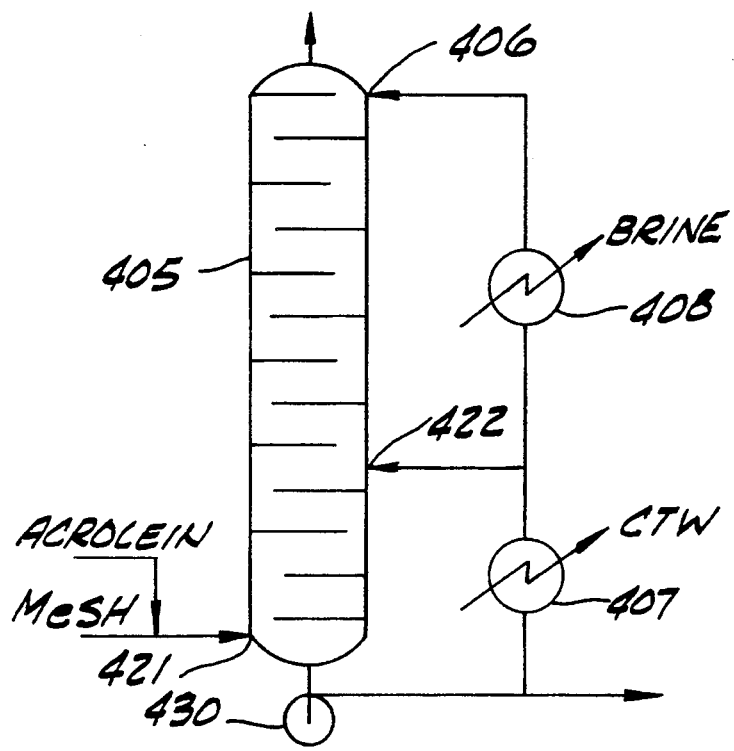
FIG. 5 is a schematic illustration of a tray column reactor for conversion of methyl mercaptan and acrolein to MMP.

Another preferred embodiment of the invention is illustrated in FIG. 5. In this embodiment, the reaction is conducted in a tray column 405. Liquid MMP reaction medium is introduced through a liquid inlet 406 at the top of column and acrolein feed gas is introduced through a gas inlet 421 at the bottom. Methyl mercaptan is also introduced at or near the bottom of the column, preferably through the same inlet 421. The interior of the column comprises a gas/liquid contact zone through which the gas and liquid phases flow countercurrently to each other, mass transfer from the gas to the liquid phase occurring primarily on the trays of the column. Reaction takes place in the liquid phase on the trays, the downcomers between trays, and in the sump at the bottom of the column. As the gas flows up the column, acrolein is progressively transferred to the liquid phase, so that gas exiting the top of the column is substantially free of acrolein and is vented through an incinerator.

Unlike the essentially isothermal gas lift reactors of FIGS. 2-4, the tray column reactor itself operates substantially adiabatically. Liquid reaction product mixture exits the bottom of the column and is divided into a product fraction which is removed from the process and a recirculating fraction which is cooled and returned to the column. A pump 430 provides the motive force for recirculation. Reaction heat is removed by transfer to cooling tower water in an indirect heat exchanger 407. In order to assure complete absorption of acrolein into the liquid phase, the recirculating MMP exiting heat exchanger 407 is preferably passed through a second indirect heat exchanger 408 where the recirculating stream is cooled to about 10° C. or lower, preferably about 0° to about 10° C., by transfer of heat to refrigerated brine. Optionally, a portion of the MMP fraction exiting cooler 407 may be recycled to port 422 at a tray in the lower portion of the column, e.g., the 6th or 8th actual tray in a 20 tray column. Although partial recycle to the lower portion of the column alters the column temperature profile, reaction occurs throughout the column in both that embodiment and in the embodiment wherein all circulating MMP reaction medium is recycled to the top of the column.

Because of the substantially adiabatic operation, a temperature gradient prevails within the column. The liquid stream within the column is heated from a temperature of about 0° C. to about 10° C. at the top of the column to a temperature of about 50° C. to about 60° C. at the bottom. Because gas exiting the column is contacted by MMP at low temperature, a favorable equilibrium prevails and acrolein recoveries >99% can be realized. Because substantially the only gas pressure drop occurs in passage of gas through the liquid held by the trays, the tray column reactor may be designed to provide a very modest backpressure on the acrolein reactor.

In the system of FIG. 5, packing instead of trays may provide the means for promoting mass transfer between the gas and liquid phases. However, a tray tower is preferred because the reaction takes place in the liquid phase, and a packed tower may not provide sufficient liquid holdup to allow the reaction to proceed to completion in the gas/liquid contact zone. If the reaction is not complete, the equilibrium distribution of acrolein between the phases may result in acrolein losses in the vent gas.

In a further alternative, the system of FIG. 5 may be operated as a bubble column. However, the pressure drop in a bubble column is substantially greater than in either a tray or packed column. In those cases where relatively high pressure drop is acceptable, a gas lift reactor is preferred because of the turbulence created in the reactor upleg.

The following examples illustrates the invention.

EXAMPLE 1

MMP was prepared by reaction of methyl mercaptan and acrolein in a gas lift reactor of the type illustrated in FIG. 2. The height of the reactor was 3 feet (0.914 m) and the upleg had an inside diameter of 0.5 in. (1.27 cm.). Gas/liquid separator 109 comprised a cylinder having an overflow port for MMP product, a connection below the liquid surface for return of circulating MMP to the downleg of the reactor loop, and a vent at the top for release of non-condensable gases. Prior to the introduction of reactants, the reactor loop was filled with MMP containing about 0.4% by weight pyridinium acetate catalyst. Circulation of MMP in the reactor was commenced by sparging air through a 1/16" orifice at acrolein feed gas inlet 123. While air was sparged to induce circulation of the MMP, hot water was passed through jacket 107 to bring the circulating MMP to a controlled temperature of 41° C.

A synthetic crude acrolein stream was prepared having the composition set forth in Table 1. This stream was introduced into the reactor through the sparger at inlet 123. Methyl mercaptan vapor was introduced through the same orifice. Acrolein and methyl mercaptan were introduced through the sparger at a molar ratio of approximately 1.0 to 1.0. The absolute rates of introduction of the reactant streams is set forth in Table 1. Also set forth in Table 1 are the superficial gas velocity in the upleg, the reactor liquid volume, the residence time of liquid product in the reactor, the recovery of reactant feeds, the reactor yields, duration of the continuous run, average supplemental catalyst feed rate, and average rate of introduction of water in the acrolein feed gas.

The sparger at inlet 123 dispersed the two reactant feeds into the liquid in the upleg and created an aerated column for this leg. As a consequence, liquid in the non-aerated downleg was forced to flow downward into the bottom of the upleg through the bottom U bend, and continue to move upward through the dispersed gases in the upleg.

Within the two-phase upleg, from the gas sparger at the bottom to the separator at the top, a reactant mixture was formed which comprised a liquid phase containing MMP, methyl mercaptan and catalyst and a gas phase containing acrolein. The acrolein and methyl mercaptan were absorbed rapidly into the liquid phase and the two absorbed reactants reacted with each other to form MMP product. The rate of reaction was very rapid, but constituted the rate limiting step of the process. Some limited vapor phase reaction between the acrolein and the mercaptan also occurred. The temperature of the gas/liquid contact zone in the upleg of the reactor was maintained at about 41° C. by removing the exothermic heat of reaction to cooling water circulated through jacket 107.

Due to the highly turbulent and well dispersed two phase flow obtained by the simple gas lift system, without mechanical agitation or a recirculating pump, the single loop reactor achieved more than 95% recovery of the total reactant feeds (i.e., acrolein and methyl mercaptan) and virtually all the recovered reactants were converted into the desired MMP product in the same reactor loop. Composition of the product and the non-condensable vent gas stream are also set forth in Table 1.

Despite the higher than usual feed impurities (propylene, propane, acetaldehyde, propionaldehyde and water) contained in the acrolein feed gas stream, little or no by-product formation or product degradation was experienced as a result of the presence of these impurities. In particular, this and other experiments demonstrated that the reaction system is capable of tolerating a water impurity content of more than 3% by volume in the acrolein feed gas stream, and the resultant >6% by weight water content that is reached in the circulating liquid during operations at steady state.

As a result of the intense mixing provided by turbulent flow in the gas/liquid contact zone, and rapid circulation of MMP reaction medium, localized hot spots or concentration imbalances are avoided. This in turn inhibits formation of undesirable by-products.

TABLE 1

EXPERIMENTAL RESULTS AND MATERIAL BALANCES
AVERAGE REACTOR TEMPERATURE = 41.00 DEG C
MOLAR FEED RATIO, ACRO./MESH = 0.99
REACTOR LIQUID VOLUME = 650.00 ML
RESIDENCE TIME OF LIQUID PRODUCT = 4.97 HRS
RECOVERY OF REACTANT FEEDS = 95.85%
REACTOR YIELDS:
WT ALDEHYDE/WT <ACR + MESH> FEED = 94.88%
MOL ALDEHYDE/MOL ACROL FEED = 94.35%
MOL ALDEHYDE/MOL MESH FEED = 94.35%
AVERAGE CATALYST FEED RATE = 0.0102 G/MIN

|  | STREAM 1 <GAS MIX IN> | | STREAM 2 <MESH INLET> | | STREAM 3 <PRODUCT OUT> | | STREAM 4 <GAS OUTLET> | |
| --- | --- | --- | --- | --- | --- | --- | --- | --- |
|  | G/MIN | W % | G/MIN | W % | G/MIN | W % | G/MIN | W % |
| O2 | 0.675 | 14.934 | 0.0 | 0.0 | 0.0 | 0.0 | 0.675 | 20.571 |
| N2 | 2.222 | 49.158 | 0.0 | 0.0 | 0.0 | 0.0 | 2.222 | 67.713 |
| CO2 | 0.074 | 1.630 | 0.0 | 0.0 | 0.0 | 0.0 | 0.074 | 2.245 |
| CO | 0.016 | 0.360 | 0.0 | 0.0 | 0.0 | 0.0 | 0.016 | 0.495 |
| PROPYLENE | 0.062 | 1.372 | 0.0 | 0.0 | 0.0 | 0.0 | 0.062 | 1.889 |
| PROPANE | 0.063 | 1.394 | 0.0 | 0.0 | 0.0 | 0.0 | 0.063 | 1.920 |
| MESH | 0.0 | 0.0 | 1.018 | 100.0 | 0.010 | 0.438 | 0.025 | 0.608 |
| ACETALD | 0.024 | 0.539 | 0.0 | 0.0 | 0.004 | 0.195 | 0.020 | 0.608 |
| PROPALD | 0.081 | 1.792 | 0.0 | 0.0 | 0.022 | 0.992 | 0.059 | 1.783 |
| ACROLEIN | 1.174 | 25.979 | 0.0 | 0.0 | 0.012 | 0.507 | 0.017 | 0.531 |
| M-ALDEH | 0.0 | 0.0 | 0.0 | 0.0 | 2.080 | 91.733 | 0.049 | 1.480 |
| CATALYST | 0.0 | 0.0 | 0.0 | 0.0 | 0.011 | 0.465 | 0.0 | 0.0 |
| WATER | 0.129 | 2.844 | 0.0 | 0.0 | 0.129 | 5.669 | 0.0 | 0.0 |
| TOTAL | 4.520 | 100.00 | 1.018 | 100.00 | 2.267 | 100.00 | 3.281 | 100.00 |
| TEMP <C> | 51.0 | | 26.0 | | 40.0 | | 40.0 | |

TABLE 1-continued

EXPERIMENTAL RESULTS AND MATERIAL BALANCES
AVERAGE REACTOR TEMPERATURE = 41.00 DEG C
MOLAR FEED RATIO, ACRO./MESH = 0.99
REACTOR LIQUID VOLUME = 650.00 ML
RESIDENCE TIME OF LIQUID PRODUCT = 4.97 HRS
RECOVERY OF REACTANT FEEDS = 95.85%
REACTOR YIELDS:
WT ALDEHYDE/WT <ACR + MESH> FEED = 94.88%
MOL ALDEHYDE/MOL ACROL FEED = 94.35%
MOL ALDEHYDE/MOL MESH FEED = 94.35%
AVERAGE CATALYST FEED RATE = 0.0102 G/MIN

| | STREAM 1 <GAS MIX IN> | | STREAM 2 <MESH INLET> | | STREAM 3 <PRODUCT OUT> | | STREAM 4 <GAS OUTLET> | |
|---|---|---|---|---|---|---|---|---|
| | G/MIN | W % | G/MIN | W % | G/MIN | W % | G/MIN | W % |
| P <PSIG> | 8.4 | | 4.8 | | 0.0 | | 0.0 | |

EXAMPLES 2–23

Using the apparatus of FIG. 2, acrolein was reacted with methyl mercaptan to produce MMP. The process was carried out in the manner generally described in Example 1, but variations were made in operating temperature, molar ratio of acrolein to methyl mercaptan in the reactor feed, overall volumetric gas feed rate, and acrolein concentration in the gas feed mixture. These process conditions and the yields for the runs of examples 2–23 are set forth in Table 2.

Measurements or determinations were made of superficial gas velocity, inlet acrolein concentration, reaction temperature, catalyst concentration, residence time, and feed ratio of acrolein to methyl mercaptan. A statistical analysis was conducted to determine the effect of the latter operating variables on productivity, acrolein recovery, yield based on acrolein, acrolein concentration in the liquid phase, and methyl mercaptan concentration in the liquid phase. The results are set forth in Table 3.

TABLE 2

| | Ex. 2 | | Ex. 3 | | Ex. 4 | |
|---|---|---|---|---|---|---|
| AVERAGE OPERATING TEMP | 40.00 | DEG C | 40.50 | DEG C | 39.00 | DEG C |
| MOLAR FEED RATIO, ACRO./MESH | 0.95 | | 0.98 | | 1.23 | |
| GAS MIXTURE FLOW TO SPARGER, STP | 3.020 | LITER/MIN | 2.826 | LITER/MIN | 2.763 | LITER/MIN |
| ACROLEIN CONC. IN GAS MIXTURE IN | 15.170 | VOL % | 9.890 | VOL % | 7.234 | VOL % |
| ACROLEIN CONC. IN OUTLET GASES | 1.360 | VOL % | 1.183 | VOL % | 1.944 | VOL % |
| SUPER. GAS VEL. IN UPLEG BOT., STP | 1.347 | FT/SEC | 1.261 | FT/SEC | 1.233 | FT/SEC |
| REACTOR LIQUID VOLUME | 886.00 | ML | 756.00 | ML | 684.00 | ML |
| RESIDENCE TIME OF LIQUID PROD. | 7.40 | HRS | 11.54 | HRS | 17.87 | HRS |
| RECOVERY OF REACTANT FEEDS | 89.68% | | 84.29% | | 75.85% | |
| REACTOR YIELDS: | | | | | | |
| WT ALDEHYDE/WT (ACR + MESH) FEED | 87.90% | | 83.22% | | 74.75% | |
| MOL ALDEHYDE/MOL ACROL FEED | 89.97% | | 84.13% | | 68.40% | |
| MOL ALDEHYDE/MOL MESH FEED | 85.59% | | 82.17% | | 83.81% | |
| DURATINO F CONTINUOUS RUN | 5.10 | HRS | 2.75 | HRS | 2.75 | HRS |
| AVERAGE CATALYST FEED RATE | 0.0105 | G/MIN | 0.0061 | G/MIN | 0.0061 | G/MIN |
| AVERAGE WATER FEED RATE | 0.0 | G/MIN | 0.0 | G/MIN | 0.0 | G/MIN |
| | Ex. 5 | | Ex. 6 | | Ex. 7 | |
| AVERAGE OPERATING TEMP | 41.00 | DEG C | 40.00 | DEG C | 40.00 | DEG C |
| MOLAR FEED RATIO, ACRO./MESH | 1.07 | | 1.26 | | 1.17 | |
| GAS MIXTURE FLOW TO SPARGER, STP | 3.128 | LITER/MIN | 3.232 | LITER/MIN | 3.249 | LITER/MIN |
| ACROLEIN CONC. IN GAS MIXTURE IN | 16.563 | VOL % | 20.648 | VOL % | 9.240 | VOL % |
| ACROLEIN CONC. IN OUTLET GASES | 2.560 | VOL % | 4.467 | VOL % | 2.417 | VOL % |
| SUPER. GAS VEL. IN UPLEG BOT., STP | 1.395 | FT/SEC | 1.441 | FT/SEC | 1.449 | FT/SEC |
| REACTOR LIQUID VOLUME | 741.00 | ML | 738.00 | ML | 760.00 | ML |
| RESIDENCE TIME OF LIQUID PROD. | 6.08 | HRS | 5.04 | HRS | 12.85 | HRS |
| RECOVERY OF REACTANT FEEDS | 87.44% | | 88.12% | | 76.32% | |
| REACTOR YIELDS: | | | | | | |
| WT ALDEHYDE/WT (ACR + MESH) FEED | 85.47% | | 85.53% | | 75.32% | |
| MOL ALDEHYDE/MOL ACROL FEED | 84.01% | | 77.31% | | 70.16% | |
| MOL ALDEHYDE/MOL MESH FEED | 89.51% | | 97.60% | | 82.36% | |
| DURATINO F CONTINUOUS RUN | 2.00 | HRS | 1.58 | HRS | 3.66 | HRS |
| AVERAGE CATALYST FEED RATE | 0.0083 | G/MIN | 0.0105 | G/MIN | 0.0068 | G/MIN |
| AVERAGE WATER FEED RATE | 0.0 | G/MIN | 0.0 | G/MIN | 0.0 | G/MIN |
| | Ex. 8 | | Ex. 9 | | Ex. 10 | |
| AVERAGE OPERATING TEMP | 45.00 | DEG C | 44.00 | DEG C | 44.00 | DEG C |
| MOLAR FEED RATIO, ACRO./MESH | 1.06 | | 1.05 | | 0.99 | |
| GAS MIXTURE FLOW TO SPARGER, STP | 3.708 | LITER/MIN | 2.538 | LITER/MIN | 3.755 | LITER/MIN |
| ACROLEIN CONC. IN GAS MIXTURE IN | 21.000 | VOL % | 29.591 | VOL % | 21.253 | VOL % |
| ACROLEIN CONC. IN OUTLET GASES | 3.005 | VOL % | 3.770 | VOL % | 1.588 | VOL % |
| SUPER. GAS VEL. IN UPLEG BOT., STP | 1.654 | FT/SEC | 1.177 | FT/SEC | 1.675 | FT/SEC |
| REACTOR LIQUID VOLUME | 734.00 | ML | 682.00 | ML | 520.00 | ML |
| RESIDENCE TIME OF LIQUID PROD. | 3.95 | HRS | 3.50 | HRS | 2.55 | HRS |
| RECOVERY OF REACTANT FEEDS | 88.95% | | 92.46% | | 91.84% | |
| REACTOR YIELDS: | | | | | | |

TABLE 2-continued

| | | | |
|---|---|---|---|
| WT ALDEHYDE/WT (ACR + MESH) FEED | 57.55% | 90.94% | 90.10% |
| MOL ALDEHYDE/MOL ACROL FEED | 85.33% | 88.82% | 90.40% |
| MOL ALDEHYDE/MOL MESH FEED | 90.26% | 93.52% | 89.73% |
| DURATINO F CONTINUOUS RUN | 3.20 HRS | 1.98 HRS | 2.40 HRS |
| AVERAGE CATALYST FEED RATE | 0.0182 G/MIN | 0.0252 G/MIN | 0.0139 G/MIN |
| AVERAGE WATER FEED RATE | 0.0 G/MIN | 0.0 G/MIN | 0.0 G/MIN |

| | Ex. 11 | Ex. 12 | Ex. 13 |
|---|---|---|---|
| AVERAGE OPERATING TEMP | 50.00 DEG C | 42.00 DEG C | 43.00 DEG C |
| MOLAR FEED RATIO, ACRO./MESH | 1.00 | 1.04 | 0.96 |
| GAS MIXTURE FLOW TO SPARGER, STP | 3.760 LITER/MIN | 3.476 LITER/MIN | 3.619 LITER/MIN |
| ACROLEIN CONC. IN GAS MIXTURE IN | 19.405 VOL % | 14.409 VOL % | 18.471 VOL % |
| ACROLEIN CONC. IN OUTLET GASES | 2.100 VOL % | 2.138 VOL % | 1.285 VOL % |
| SUPER. GAS VEL. IN UPLEG BOT., STP | 1.677 FT/SEC | 1.550 FT/SEC | 1.703 FT/SEC |
| REACTOR LIQUID VOLUME | 527.00 ML | 529.00 ML | 649.00 ML |
| RESIDENCE TIME OF LIQUID PROD. | 2.89 HRS | 4.31 HRS | 3.51 HRS |
| RECOVERY OF REACTANT FEEDS | 89.52% | 87.37% | 92.64% |
| REACTOR YIELDS: | | | |
| WT ALDEHYDE/WT (ACR + MESH) FEED | 88.01% | 85.57% | 90.52% |
| MOL ALDEHYDE/MOL ACROL FEED | 88.18% | 83.97% | 92.07% |
| MOL ALDEHYDE/MOL MESH FEED | 87.80% | 87.48% | 88.76% |
| DURATINO F CONTINUOUS RUN | 2.65 HRS | 2.48 HRS | 2.13 HRS |
| AVERAGE CATALYST FEED RATE | 0.0346 G/MIN | 0.0097 G/MIN | 0.0195 G/MIN |
| AVERAGE WATER FEED RATE | 0.0 G/MIN | 0.0571 G/MIN | 0.0 G/MIN |

| | Ex. 14 | Ex. 15 | Ex. 16 |
|---|---|---|---|
| AVERAGE OPERATING TEMP | 55.00 DEG C | 41.00 DEG C | 45.00 DEG C |
| MOLAR FEED RATIO, ACRO./MESH | 1.01 | 0.97 | 1.01 |
| GAS MIXTURE FLOW TO SPARGER, STP | 3.946 LITER/MIN | 2.924 LITER/MIN | 3.124 LITER/MIN |
| ACROLEIN CONC. IN GAS MIXTURE IN | 18.137 VOL % | 16.049 VOL % | 18.547 VOL % |
| ACROLEIN CONC. IN OUTLET GASES | 2.322 VOL % | 0.503 VOL % | 2.429 VOL % |
| SUPER. GAS VEL. IN UPLEG BOT., STP | 1.760 FT/SEC | 1.304 FT/SEC | 1.393 FT/SEC |
| REACTOR LIQUID VOLUME | 525.00 ML | 650.00 ML | 600.00 ML |
| RESIDENCE TIME OF LIQUID PROD. | 3.07 HRS | 4.97 HRS | 4.13 HRS |
| RECOVERY OF REACTANT FEEDS | 85.35% | 94.22% | 86.24% |
| REACTOR YIELDS: | | | |
| WT ALDEHYDE/WT (ACR + MESH) FEED | 83.94% | 92.34% | 84.06% |
| MOL ALDEHYDE/MOL ACROL FEED | 83.58% | 93.79% | 83.84% |
| MOL ALDEHYDE/MOL MESH FEED | 84.36% | 90.68% | 84.31% |
| DURATINO F CONTINUOUS RUN | 2.27 HRS | 4.88 HRS | 4.42 HRS |
| AVERAGE CATALYST FEED RATE | 0.0162 G/MIN | 0.0102 G/MIN | 0.0113 G/MIN |
| AVERAGE WATER FEED RATE | 0.0 G/MIN | 0.0922 G/MIN | 0.1018 G/MIN |

| | Ex. 17 | Ex. 18 | Ex. 19 |
|---|---|---|---|
| AVERAGE OPERATING TEMP | 42.00 DEG C | 40.00 DEG C | 39.00 DEG C |
| MOLAR FEED RATIO, ACRO./MESH | 0.95 | 1.06 | 1.13 |
| GAS MIXTURE FLOW TO SPARGER, STP | 3.238 LITER/MIN | 2.481 LITER/MIN | 2.073 LITER/MIN |
| ACROLEIN CONC. IN GAS MIXTURE IN | 15.622 VOL % | 25.019 VOL % | 29.440 VOL % |
| ACROLEIN CONC. IN OUTLET GASES | 0.961 VOL % | 3.160 VOL % | 2.772 VOL % |
| SUPER. GAS VEL. IN UPLEG BOT., STP | 1.444 FT/SEC | 1.106 FT/SEC | 0.925 FT/SEC |
| REACTOR LIQUID VOLUME | 880.00 ML | 800.00 ML | 800.00 ML |
| RESIDENCE TIME OF LIQUID PROD. | 6.60 HRS | 5.48 HRS | 5.14 HRS |
| RECOVERY OF REACTANT FEEDS | 92.06% | 86.71% | 96.40% |
| REACTOR YIELDS: | | | |
| WT ALDEHYDE/WT (ACR + MESH) FEED | 8909% | 82.06% | 93.72% |
| MOL ALDEHYDE/MOL ACROL FEED | 91.38% | 79.94% | 88.76% |
| MOL ALDEHYDE/MOL MESH FEED | 86.53% | 84.65% | 100.23% |
| DURATINO F CONTINUOUS RUN | 5.33 HRS | 5.40 HRS | 4.00 HRS |
| AVERAGE CATALYST FEED RATE | 0.0134 G/MIN | 0.0157 G/MIN | 0.0167 G/MIN |
| AVERAGE WATER FEED RATE | 0.0 G/MIN | 0.0 G/MIN | 0.0 G/MIN |

| | Ex. 20 | Ex. 21 | Ex. 22 |
|---|---|---|---|
| AVERAGE OPERATING TEMP | 37.00 DEG C | 43.00 DEG C | 46.00 DEG C |
| MOLAR FEED RATIO, ACRO./MESH | 0.94 | 0.70 | 1.25 |
| GAS MIXTURE FLOW TO SPARGER, STP | 2.259 LITER/MIN | 2.440 LITER/MIN | 2.531 LITER/MIN |
| ACROLEIN CONC. IN GAS MIXTURE IN | 26.870 VOL % | 27.026 VOL % | 33.558 VOL % |
| ACROLEIN CONC. IN OUTLET GASES | 1.850 VOL % | −2.753 VOL % | 12.143 VOL % |
| SUPER. GAS VEL. IN UPLEG BOT., STP | 1.008 FT/SEC | 1.088 FT/SEC | 1.129 FT/SEC |
| REACTOR LIQUID VOLUME | 850.00 ML | 765.00 ML | 792.00 ML |
| RESIDENCE TIME OF LIQUID PROD. | 5.25 HRS | 3.83 HRS | 4.95 HRS |
| RECOVERY OF REACTANT FEEDS | 92.91% | 92.23% | 74.65% |
| REACTOR YIELDS: | | | |
| WT ALDEHYDE/WT (ACR + MESH) FEED | 90.42% | 88.57% | 71.13% |
| MOL ALDEHYDE/MOL ACROL FEED | 93.31% | 105.97% | 64.65% |
| MOL ALDEHYDE/MOL MESH FEED | 87.25% | 74.33% | 80.53% |
| DURATINO F CONTINUOUS RUN | 3.00 HRS | 2.40 HRS | 1.40 HRS |
| AVERAGE CATALYST FEED RATE | 0.0139 G/MIN | 0.0069 G/MIN | 0.0 G/MIN |
| AVERAGE WATER FEED RATE | 0.0 G/MIN | 0.0 G/MIN | 0.0 G/MIN |

| | Ex. 23 |
|---|---|
| AVERAGE OPERATING TEMP | 39.00 DEG C |

TABLE 2-continued

| | |
|---|---|
| MOLAR FEED RATIO, ACRO./MESH | 0.63 |
| GAS MIXTURE FLOW TO SPARGER, STP | 2.276 LITER/MIN |
| ACROLEIN CONC. IN GAS MIXTURE IN | 19.476 VOL % |
| ACROLEIN CONC. IN OUTLET GASES | −1.573 VOL % |
| SUPER. GAS VEL. IN UPLEG BOT., STP | 1.015 FT/SEC |
| REACTOR LIQUID VOLUME | 792.00 ML |
| RESIDENCE TIME OF LIQUID PROD. | 5.65 HRS |
| RECOVERY OF REACTANT FEEDS | 91.16% |
| REACTOR YIELDS: | |
| WT ALDEHYDE/WT (ACR + MESH) FEED | 82.88% |
| MOL ALDEHYDE/MOL ACROL FEED | 105.03% |
| MOL ALDEHYDE/MOL MESH FEED | 66.51% |
| DURATINO F CONTINUOUS RUN | 5.00 HRS |
| AVERAGE CATALYST FEED RATE | 0.0 G/MIN |
| AVERAGE WATER FEED RATE | 0.0 G/MIN |

TABLE 3

EXPERIMENTAL RESULTS ON THE EFFECTS OF OPERATING VARIABLES

| | VARIABLES | | | | | | RESULTS | | | | |
|---|---|---|---|---|---|---|---|---|---|---|---|
| RUN NO. | VG (F/S) | YA (M %) | T (C) | CC (W %) | TR (HR) | A/M (RATIO) | PR (G/M) | REC (%) | YIELD (%) | CA (W %) | CM (W %) |
| 041684 (TYPICAL) | 1.30 | 16.1 | 41 | .47 | 5.0 | 0.97 | 2.27 | 94.2 | 92.3 | 0.51 | 1.34 |
| 010984A | 1.02 | 19.5 | 39 | 0.4 | 5.7 | 0.63 | 2.34 | 91.2 | 82.9 | .051 | 8.85 |
| 011984B | 1.13 | 33.6 | 46 | 0.4 | 5.0 | 1.25 | 2.77 | 74.7 | 71.1 | 4.35 | 0.20 |
| 042584 | 1.76 | 18.1 | 55 | 0.4 | 3.1 | 1.01 | 2.94 | 85.4 | 83.9 | 1.30 | 0.28 |
| 050284 | 1.68 | 19.4 | 50 | 0.7 | 2.9 | 1.00 | 3.13 | 89.5 | 88.0 | 0.05 | 1.60 |
| 061384B | 1.44 | 20.7 | 40 | .39 | 5.0 | 1.26 | 2.54 | 88.1 | 85.5 | 2.43 | 0.43 |
| 061384A | 1.40 | 16.6 | 41 | .32 | 6.1 | 1.07 | 2.11 | 87.4 | 86.5 | .158 | .913 |
| 052384 | 1.45 | 9.24 | 40 | .43 | 12.8 | 1.17 | 1.03 | 76.3 | 75.3 | .775 | .487 |
| 061484B | 1.23 | 7.23 | 39 | .39 | 17.9 | 1.23 | 0.66 | 75.9 | 74.8 | 1.12 | .291 |

VG = SUPERFICIAL GAS VELOCITY, FT/SEC
YA = INLET ACROLEIN CONC., MOLE %
T = REACTOR TEMPERATURE, DEG. C
CC = CATALYST (PYRIDINE ACETATE) CONC., WT. %
TR = RESIDENCE TIME BASED ON PRODUCT RATE, HOUR
A/M = FEED RATIO OF ACROLEIN TO MESH, MOLE RATIO
PR = THE RATE OF PRODUCT MADE, G/MIN
REC = PERCENT ACROLEIN RECOVERED FROM FEED, %
YIELD = PERCENT FEED ACROLEIN CONVERTED TO ALDEHYDE PRODUCT, %
CA = ACROLEIN CONC. IN LIQUID, WT. %
CM = MESH CONC. IN LIQUID, WT. %

EXAMPLE 24

Using a process of the type illustrated in FIG. 2, a 50 hour continuous run was conducted with an acrolein feed gas produced by catalytic oxidation of propylene in a laboratory reactor. During the run, the temperature of the gas lift loop was controlled at about 40° C. and the acrolein to methyl mercaptan feed ratio was constantly monitored by means of a discrete gas chromatography analysis of a reactor liquid sample every half hour. The final aldehyde product had the following composition:

| | |
|---|---|
| Acetaldehyde | 0.11 wt. % |
| Methyl Mercaptan | 0.88 |
| Acrolein | 0.07 |
| Allyl Alcohol | 0.29 |
| Acetic Acid | 0.35 |
| Acrylic Acid | 0.52 |
| $\beta$-hydroxypropionaldehyde | 0.27 |
| Pyridine | 0.19 |
| MMP | 89.02 |
| By-product having MW = 190 | 0.18 |
| Water | 7.00 |

In a commercial operation in which water is controlled to a more typical level, e.g., 2% the MMP assay would be greater than 94% The relatively high proportion of $\beta$-hydroxypropionaldehyde was a result of the presence of water at well above the level readily achievable by cooling the acrolein feed gas in a commercial process.

EXAMPLE 25

Using a process of the type illustrated in FIG. 2, comparative tests were conducted on a wetted wall reactor and a horizontal loop reactor. A synthetic acrolein feed gas was used in these runs. During steady state operation, liquid product samples were analyzed by gas chromatography to determine aldehyde assay, residual acrolein, methyl mercaptan and by-product impurities. Based on these analyses, calculations were made to determine the percent acrolein recovery, product yield and reactor material balance for each run. Average mass transfer coefficient and reaction kinetic rate constants were obtained by fitting experimental data to a two-phase reactor model. Gas holdup and liquid recirculation rate data were also measured and correlated.

Physical dimensions of the reactor systems are set forth in Table 4, together with the temperature, gas rate and liquid rate for each run. A comparison of reaction conditions, feed rates, yields, and average mass transfer coefficients is set forth in Table 5.

TABLE 4

REACTOR SIZES AND OPERATING VARIABLES

| REACTOR | TUBE SIZE | SEPARATOR | TEMP. | GAS RATE | LIQUID RATE |
| --- | --- | --- | --- | --- | --- |
| Gas-lift | .5" id × 3.5' (or 5' w/spool) | 2.5" od × 8" | 35–55 C | 2.2–4.0 l/m | 4.0–12 l/m |
| Wetted Wall | .5" id × 4.5' | 4" od × 6" | 30–48 C | 3.0–6.5 l/m | .6–.8 l/m |
| Horiz. Loop | .5" id × 7.5' | —3" od × 11" 4" od × 13" | 37–40 C | 2.5–3.4 l/m | 9.5–13.3 l/m |

TABLE 5

TYPICAL RESULTS OF REACTOR TESTED

| | GAS LIFT | WETTED WALL | HORIZ. LOOP |
| --- | --- | --- | --- |
| Run No. | 041684 | 110184 | 011685 |
| Inlet Gas Conc. Vol % acrol. | 16.0 | 16.8 | 17.3 |
| Outlet Gas Conc. Vol % acrol. | 0.503 | 1.92 | 3.82 |
| Reactor Temp., C | 41.0 | 36.0 | 40.0 |
| Superficial Vel. | | | |
| Gas, f/s | 1.304 | 1.46 | 1.39 |
| Liq., f/s | 3.5 | 0.3 | 5.7 |
| Liquid Conc. | | | |
| Wt. % acrol. | 0.51 | 0.71 | 0.05 |
| Wt. % MeSH | 1.30 | 0.20 | 1.35 |
| Gas Mixture Feed Rate, g/m | 4.43 | 4.84 | 4.56 |
| Acrol. Feed Rate, g/m | 1.174 | 1.372 | 1.352 |
| MeSH Vap. Feed Rate, g/m | 1.042 | 1.160 | 1.095 |
| Aldehyde Product Rate, g/m | 2.267 | 2.306 | 2.118 |
| Feed Recovery (acrol. + MeSH), wt. % | 94.2 | 88.2 | 82.1 |
| Reactor Yield (ald./acr + MeSH, wt. % | 92.34 | 87.33 | 80.97 |
| Ave. Mass Transfer Coeff., mol/l-atm-h | 150 | 120 | 50 |

EXAMPLE 26

In accordance with the process illustrated in FIG. 5, a reaction medium comprising MMP and methyl mercaptan is contacted with an acrolein vapor stream in a tray column containing 20 trays. None of the MMP reaction medium exiting cooler 407 is recycled to the bottom portion of the tower. Instead, all of the circulating MMP is passed through cooler 308 and recycled to the top of the column. The acrolein vapor stream is introduced into the bottom of the column at a rate of 662.4 lb. moles per hour, and contains 15% by volume acrolein, 0.28% by volume acetaldehyde, 17% by volume water vapor, and 83% by volume non-condensables. Methyl mercaptan is introduced into the bottom of the column at a rate of 100 lb. moles/hr.

MMP reaction medium is introduced into the top of the column at a rate of about 600 lb. moles/hr. An MMP product stream containing 97.3% by weight MMP is removed from the process in the column at a rate of about 110.4 lb. moles/hr.

What is claimed is:

1. A process for the continuous preparation of 3-(methylthio)propanal, comprising:

contacting a liquid reaction medium with a gaseous acrolein feed stream in a gas/liquid contact zone, said reaction medium containing 3-(methylthio)propanal, methyl mercaptan and a catalyst for the reaction between methyl mercaptan and acrolein, said gaseous acrolein feed stream comprising acrolein vapor and non-condensable gas;

causing said feed stream and said reaction medium to flow co-currently through said contact zone, whereby acrolein is transferred from said feed stream to said reaction medium and reacts with methyl mercaptan in said medium to produce a liquid reaction product containing 3-(methylthio)propanal; separating said non-condensable gas from said liquid reaction product;

dividing said reaction product into a product fraction and a circulating fraction; and recycling said circulating fraction to said gas/liquid contact zone.

2. A process as set forth in claim 1 wherein said gaseous acrolein stream, methyl mercaptan, and said reaction medium are mixed to prepare a heterogeneous reactant mixture in which acrolein is distributed between a liquid phase and a gas phase, said liquid phase containing 3-(methylthio)propanal, methyl mercaptan and catalyst, and said gas phase containing non-condensable gas;

said heterogeneous reactant mixture is passed through said gas/liquid contact zone at a temperature effective for direct reaction between methyl mercaptan and acrolein to produce 3-(methylthio)propanal, thereby producing a heterogeneous reaction product mixture comprising liquid 3-(methylthio)propanal and non-condensable gas;

said non-condensable gas is separated from the 3-(methylthio)propanal of said reaction product mixture;

the 3-(methylthio)propanal of said reaction product mixture is divided into a product fraction and a circulating fraction; and said circulating fraction is recycled to said gas/liquid contact zone.

3. A process as set forth in claim 2 wherein said heterogeneous reaction mixture is passed under turbulent conditions through said contact zone.

4. A process as set forth in claim 2 wherein methyl mercaptan and acrolein are continuously introduced into said reaction medium in a molar ratio sufficiently close to 1.0 so that 3-(methylthio)propanal is produced by direct reaction between methyl mercaptan and acrolein, substantially without formation of the hemi(methylthio)acetal of 3-(methylthio)propanal.

5. A process as set forth in claim 4 wherein said reactant mixture is substantially free of the hemi(methylthio)acetal of 3-(methylthio)propanal.

6. A process as set forth in claim 2 wherein methyl mercaptan and acrolein are continuously introduced into said reaction medium in a molar ratio of methyl mercaptan to acrolein between about 0.95 and about 1.2.

7. A process as set forth in claim 6 wherein methyl mercaptan and acrolein are continuously introduced into said reaction medium in a molar ratio of methyl mercaptan to acrolein between about 1.0 and about 1.02.

8. A process as set forth in claim 2 wherein said gaseous acrolein feed stream comprises a treated gas stream obtained from the catalytic oxidation of propylene, the treatment comprising removal of acrylic acid from the crude gas stream produced in the oxidation.

9. A process as set forth in claim 8 wherein said treatment comprises cooling the crude gas stream for condensation and removal of acrylic acid and water therefrom.

10. A process as set forth in claim 9 wherein said gaseous acrolein feed stream contains between about 5% and about 25% by volume acrolein, between about 2% and about 8% by volume water vapor, up to about 0.5% by volume acetaldehyde, up to about 0.1% by volume acrylic acid, up to about 1.0% by volume propylene, up to about 1.0% by volume propane, up to about 1.0% by volume propionaldehyde, and between about 60% and about 80% by volume non-condensables.

11. A process as set forth in claim 2 wherein the reaction is conducted in a gas lift reactor, said gas lift reactor comprising an upflow conduit containing said gas/liquid contact zone, a downflow conduit in fluid flow communication at its lower end with the lower end of the upflow conduit, and a gas/liquid separation zone between and in fluid flow communication with the upper ends of the upflow conduit and the downflow conduit, said acrolein feed stream being introduced into said upflow conduit at or near the lower end thereof, non-condensable gas being separated from the reaction product mixture in said separation zone, and said circulating fraction being recycled to said gas/liquid contact zone by flowing through said downflow conduit.

12. A process as set forth in claim 11 wherein said gas/liquid contact zone is cooled to maintain the temperature of the reaction between about 30° C. and about 70° C.

13. A process as set forth in claim 12 wherein said gas/liquid contact zone is cooled to maintain the temperature of the reaction between about 40° C. and about 50° C.

14. A process as set forth in claim 12 wherein the total pressure in said gas/liquid contact zone is between about atmospheric and about 2 atm.

15. A process as set forth in claim 11 wherein the gas phase is dispersed in a continuous liquid phase in said gas/liquid contact zone.

16. A process as set forth in claim 11 wherein the flow pattern in said upflow conduit is bubble flow or slug flow.

17. A process as set forth in claim 16 wherein the superficial gas flow velocity in said upflow leg is between about 0.1 and about 0.5 m/sec., and the superficial liquid flow velocity in said upflow leg is between about 0.3 and about 3.0 m/sec.

18. A process as set forth in claim 16 wherein the gas phase is in substantially plug flow through said gas/liquid contact zone and the liquid phase is substantially backmixed throughout said reactor.

19. A process as set forth in claim 11 wherein methyl mercaptan and said gaseous acrolein feed stream are both introduced into the reactor substantially at the lower end of said upflow conduit.

20. A process as set forth in claim 11 wherein said acrolein feed gas is introduced into said reactor substantially at the lower end of said upflow conduit, and methyl mercaptan is introduced into recycle 3-(methylthio)propanal in said downflow conduit.

21. A process as set forth in claim 1 wherein the catalyst is selected from the group consisting of organic amines and mixtures of organic amines and organic acids.

22. A process for the continuous preparation of 3-(methylthio)propanal, comprising:
contacting a liquid reaction medium with a gaseous acrolein feed stream in a gas/liquid contact zone, said reaction medium containing 3-(methylthio)propanal, methyl mercaptan and a catalyst for the reaction between methyl mercaptan and acrolein, said gaseous acrolein feed stream comprising acrolein vapor, non-condensable gas and not more than about 8% by volume water vapor, whereby acrolein is transferred from said feed stream to said reaction medium and reacts with methyl mercaptan in said medium to produce a liquid reaction product containing 3-(methylthio)propanal;
separating said non-condensable gas from said liquid reaction product;
dividing said reaction product into a product fraction and a circulating fraction; and
recycling said circulating fraction to said gas/liquid contact zone.

23. A process as set forth in claim 22 wherein said gaseous acrolein feed stream and said reaction medium are passed countercurrently-through a vertical column containing means for promoting mass transfer between the gas phase and the liquid phase, non-condensable gas is vented from the top of said column, and liquid reaction product is withdrawn from the bottom of said column.

24. A process as set forth in claim 23 wherein said circulating stream is cooled by indirect heat exchange to remove exothermic reaction heat from the reaction medium.

25. A process as set forth in claim 24 wherein said circulating stream is cooled to a temperature of not greater than about 10° C. to promote absorption of acrolein in said reaction medium in the upper portion of said column.

26. A process as set forth in claim 23 wherein said mass transfer means comprises gas/liquid contacting trays of a tray column.

27. A process as set forth in claim 22 wherein said gaseous acrolein stream, methyl mercaptan, and said reaction medium are mixed to prepare a heterogeneous reactant mixture in which acrolein is distributed between a liquid phase and a gas phase, said liquid phase containing 3-(methylthio)propanal, methyl mercaptan and catalyst, and said gas phase containing non-condensable gas;
said heterogeneous reactant mixture is passed through said gas/liquid contact zone at a temperature effective for direct reaction between methyl mercaptan and acrolein to produce 3-(methylthio)propanal, thereby producing a heterogeneous reaction product mixture comprising liquid 3-(methylthio)propanal and non-condensable gas;
said non-condensable gas is separated from the 3-(methylthio)propanal of said reaction product mixture;
the 3-(methylthio)propanal of said reaction product mixture is divided into a product fraction and a circulating fraction; and
said circulating fraction is recycled to said gas/liquid contact zone.

28. A process as set forth in claim 27 wherein methyl mercaptan and acrolein are continuously introduced into said reaction medium in a molar ratio sufficiently close to 1.0 so that 3-(methylthio)propanal is produced by direct reaction between methyl mercaptan and acrolein, substantially without formation of the hemi(methylthio)acetal of 3-(methylthio)propanal.

29. A process as set forth in claim 28 wherein said reactant mixture is substantially free of the hemi(methylthio)acetal of 3-(methylthio)propanal.

30. A process as set forth in claim 27 wherein said gaseous acrolein feed stream comprises a treated gas stream obtained from the catalytic oxidation of propylene, the treatment comprising removal of acrylic acid from the crude gas stream produced in the oxidation.

31. A process as set forth in claim 30 wherein said gaseous acrolein feed stream contains between about 5% and about 25% by volume acrolein, between about 2% and about 8% by volume water vapor, up to about 0.5% by volume acetaldehyde, up to about 0.1% by volume acrylic acid, up to about 1.0% by volume propylene, up to about 1.0% by volume propane, up to about 1.0% by volume propionaldehyde, and between about 60% and about 80% by volume non-condensables.

32. A process for the continuous preparation of 3-(methylthio)propanal, comprising:

contacting a liquid reaction medium with a gaseous acrolein feed stream in a gas/liquid contact zone, said reaction medium containing 3-(methylthio)propanal, methyl mercaptan and a catalyst for the reaction between methyl mercaptan and acrolein, said gaseous acrolein feed stream comprising acrolein vapor and non-condensable gas, the relative proportions of acrolein and methyl mercaptan entering said contact zone being substantially stoichiometrically equivalent, whereby acrolein is transferred from said feed stream to said reaction medium and reacts directly with methyl mercaptan in said medium without substantial formation of the intermediate hemi(methylthio)acetal of 3-(methylthio)propanal to produce a liquid reaction product containing 3-(methylthio)propanal;

separating said non-condensable gas from said liquid reaction product;

dividing said reaction product into a product fraction and a circulating fraction; and recycling said circulating fraction to said gas/liquid contact zone.

33. A process as set forth in claim 32 wherein the rate of said reaction is at least about three times greater than the rate of reaction would have been under otherwise the same conditions if the reaction were allowed to proceed through the intermediate hemi(methylthio)acetal.

34. A process for the continuous preparation of 3-(methylthio)propanal, comprising:

contacting a liquid reaction medium with a gaseous acrolein feed stream in a gas/liquid contact zone through which said feed stream and said reaction medium are passed countercurrently, said reaction medium containing 3-(methylthio)propanal, methyl mercaptan and a catalyst for the reaction between methyl mercaptan and acrolein, said gaseous acrolein feed stream comprising acrolein vapor and non-condensable gas, whereby acrolein is transferred from said feed stream to said reaction medium and reacts with methyl mercaptan in said medium to produce a liquid reaction product containing 3-(methylthio)propanal, the liquid holdup in said countercurrent gas/liquid contact zone being sufficient so that the reaction between methyl mercaptan and acrolein proceeds substantially to completion within said zone;

separating said non-condensable gas from said liquid reaction product;

dividing said reaction product into a product fraction and a circulating fraction; and recycling said circulating fraction to said gas/liquid contact zone.

35. A process as set forth in claim 34 wherein said gas/liquid contact zone comprises a tray column reactor.

36. A process as set forth in claim 34 wherein the total pressure in said gas/liquid contact zone is not greater than about 2 atmospheres.

* * * * *